United States Patent [19]

Sandoval et al.

[11] Patent Number: 5,326,738
[45] Date of Patent: Jul. 5, 1994

[54] STABLE, COVALENTLY-BONDED SUPPORTS FOR CHEMICAL SEPARATION APPARATUS MADE THROUGH A HYDRIDE INTERMEDIATE

[76] Inventors: Junior E. Sandoval, 4231 Norwalk Dr. #EE 311, San Jose, Calif. 95129; Joseph J. Pesek, 4142 Rosenbaum Ave., San Jose, Calif. 95136

[21] Appl. No.: 838,429
[22] PCT Filed: Sep. 13, 1990
[86] PCT No.: PCT/US90/05202
§ 371 Date: Mar. 9, 1992
§ 102(e) Date: Mar. 9, 1992
[87] PCT Pub. No.: WO91/04095
PCT Pub. Date: Apr. 4, 1991

Related U.S. Application Data

[63] Continuation-in-part of Ser. No. 407,816, Sep. 15, 1989, Pat. No. 5,017,540.

[51] Int. Cl.⁵ .................. B01J 20/06; B01J 20/22; B01J 20/30
[52] U.S. Cl. .................. 502/401; 502/158; 502/407; 502/414
[58] Field of Search .............. 502/401, 158, 407, 414

[56] References Cited

U.S. PATENT DOCUMENTS

| | | | |
|---|---|---|---|
| 2,705,222 | 3/1955 | Wagner | 252/188.26 |
| 3,839,385 | 10/1974 | Meiller et al. | 502/158 |
| 3,950,269 | 4/1976 | Setterquist | 502/154 |
| 3,956,179 | 5/1976 | Sebestian et al. | 502/158 |
| 4,257,916 | 3/1981 | Hancock et al. | 502/60 |
| 4,324,873 | 4/1982 | Wada et al. | 502/158 |
| 4,335,022 | 6/1982 | Slaugh | 502/263 |
| 4,467,048 | 8/1984 | Johnson | 502/246 |
| 4,555,395 | 11/1985 | Sirovich et al. | 423/644 |
| 4,661,248 | 4/1987 | Ramsden et al. | 210/198.2 |
| 4,680,201 | 7/1987 | Hjerten | 427/230 |
| 4,701,430 | 10/1987 | Jung et al. | 502/159 |
| 4,705,725 | 11/1987 | Glajch et al. | 502/407 |
| 4,746,572 | 5/1988 | Glajch et al. | 502/407 |
| 4,828,695 | 5/1989 | Yamamura et al. | 502/401 |
| 4,904,632 | 2/1990 | Pesek et al. | 502/401 |
| 4,946,818 | 8/1990 | Lewis | 502/158 |
| 4,959,340 | 9/1990 | Williams | 502/401 |
| 5,017,540 | 5/1991 | Sandoval et al. | 502/158 |
| 5,203,991 | 4/1993 | Katsuna et al. | 502/401 |

FOREIGN PATENT DOCUMENTS

215884 11/1965 U.S.S.R. .................. 556/430

OTHER PUBLICATIONS

Deuel et al., "119. Organische Derivate des Silikagels mit Si-O-C-Bindung I", *Helvetica Chimica Acta*, vol. 42, No. 119, pp. 1160–1165, 1959.

Slinyakova et al., "Adsorption and other properties of a hydrogen-silica adsorbent with Si-H bond (polysiloxane hydride xerogel)", *Kolloidn. Zh.*, vol. 27, No. 5, pp. 758–764, 1965. (English abstract/translation provided.)

Budkevich et al., "Reduction properties of hydridepolysiloxane xerogel", *Kolloidn. Zh.*, vol. 28, No. 1, pp. 21–26, 1966. (English abstract provided.)

Slinyakova et al., "An investigation of adsorptive properties of ethylphenyl and hydridopolysiloxanes by gas chromatography", *Ukr. Khim. Zh.*, vol. 33, No. 4, pp. 373–376, 1967. (English abstract provided.)

(List continued on next page.)

*Primary Examiner*—Carl F. Dees
*Attorney, Agent, or Firm*—Majestic, Parsons, Siebert & Hsue

[57] ABSTRACT

The present invention produces very stable, covalently bonded separation substrates for separations application such as liquid and gas chromatography as well as capillary zone electrophoresis. An intermediate substrate is prepared which has hydride species on the substrate surface. These hydrides preferably are further derivatized by the catalytic addition of organic compounds bearing a terminal vinyl group. The final surface modification contains closely packed, direct carbon linkages that are stable.

15 Claims, 6 Drawing Sheets

OTHER PUBLICATIONS

Kol'tsov et al., "The effect of the degree of dehydration of silica gel on the mechanism of hydrolysis of trichlorosilane", *Russian Journal of Physical Chemistry*, vol. 41, No. 3, pp. 336–337, Mar. 1967.

Morterra et al., "Reactive Silica. I. The Formation of a Reactive Silica by the Thermal Collapse of the Methoxy Groups of Methylated Aerosil", *J. Phsy. Chem.*, vol. 73, No. 2, pp. 321–326, Feb. 1969.

Morterra et al., "Reactive Silica. II. The Nature of the Surface Silicon Hydrides Produced by the Chemisorption of Hydrogen", *J. Phys. Chem.*, vol. 73, No. 2, pp. 327–333, Feb. 1969.

Halasz et al., "New Stationary Phase for Chromatography", *Angew. Chem. internat. Edit.*, vol. 8, No. 6, pp. 453–454, 1969.

Budkevich et al., "Adsorption of various substances from their solution in hexane and carbon tetrachloride on hydride-polysiloxane xerogel and silica gel", *Kolloidn. Zh.*, vol. 32, No. 1, pp. 17–23, 1970. (English abstract.)

Budkevich et al., "Thermooxidative degradation of hydridopolysiloxane xerogel", *Kur. Khim. Zh.*, vol. 37, No. 5, pp. 429–433, 1971. (English abstract provided.)

Roumeliotis et al., "Structure and Properties of n-Alkyldimethylsilyl Bonded Silica Reversed-Phase Packings", *Journal of Chromatography*, vol. 149, pp. 211–224, 1978.

Speier, "Homogeneous Catalysis of Hydrosilation by Transition Metals", *Advances in Organometallic Chemistry*, vol. 17, pp. 407–447, 1979.

Jorgenson et al., "Capillary Zone Electrophoresis", *Science*, vol. 222, pp. 266–272, Oct. 21, 1983.

Kirkland et al., "Liquid Phase Separation Methods: HPLC, FFFF, Electrophoresis", *Chromatographia*, vol. 24, pp. 58–76, 1987.

Sandoval et al., "Synthesis and Characterization of a Hydride-Modified Porous Silica Material as an Intermediate in the Preparation of Chemically Bonded Chromatographic Stationary Phases," *Analytical Chemistry*, vol. 61, No. 18, pp. 2067–2075, Sep. 15, 1989.

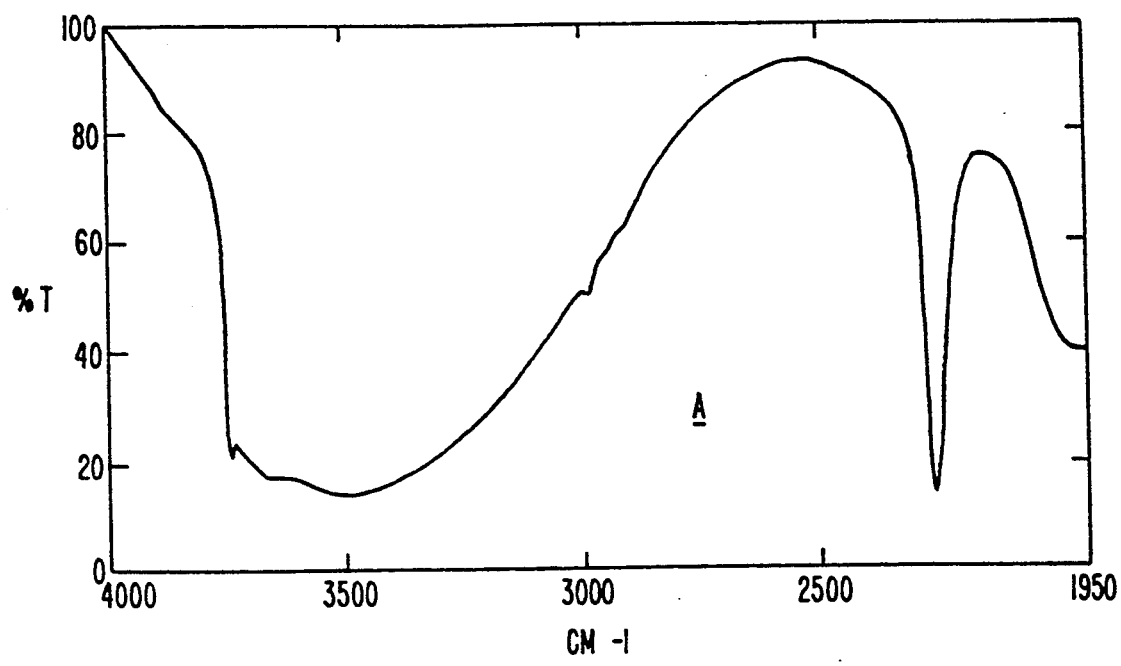
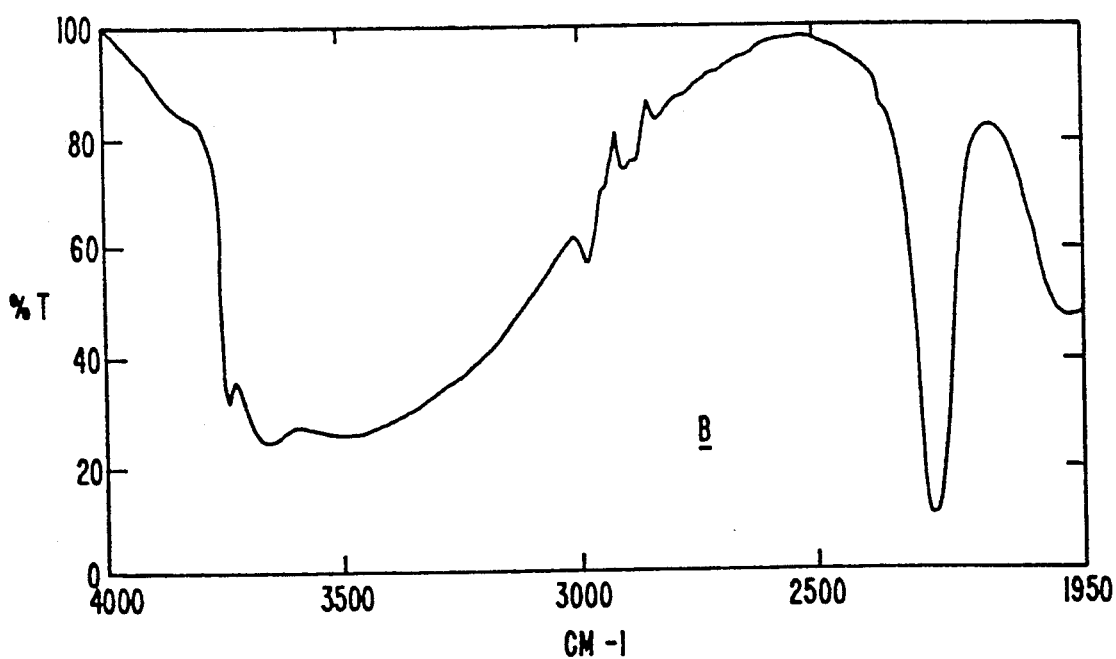
FIG._1.

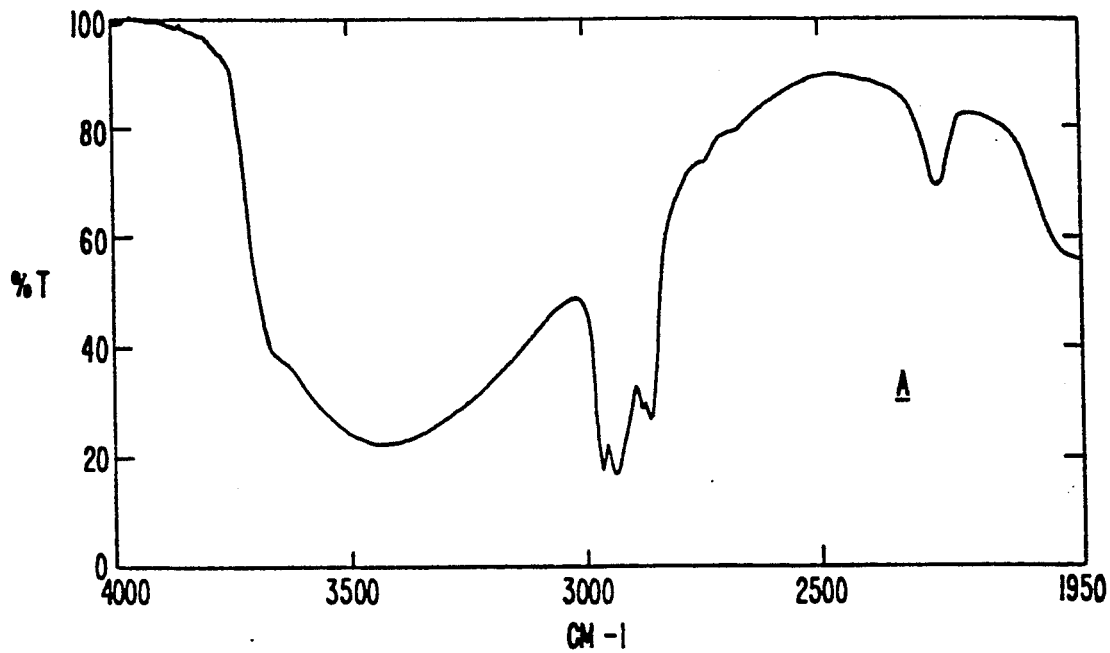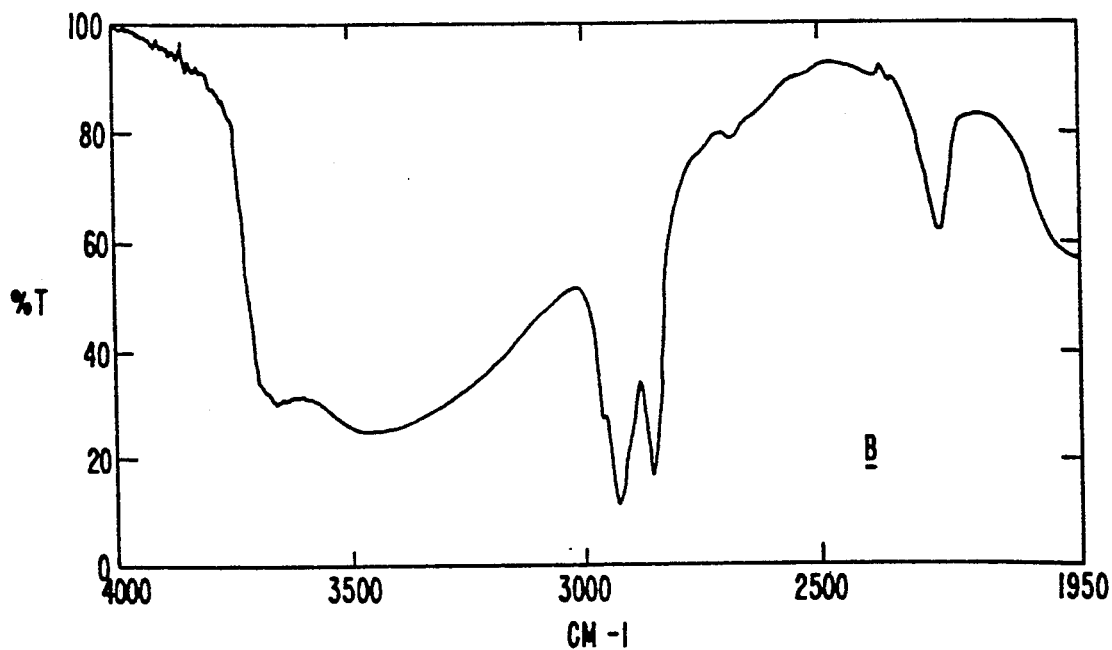
FIG._2.

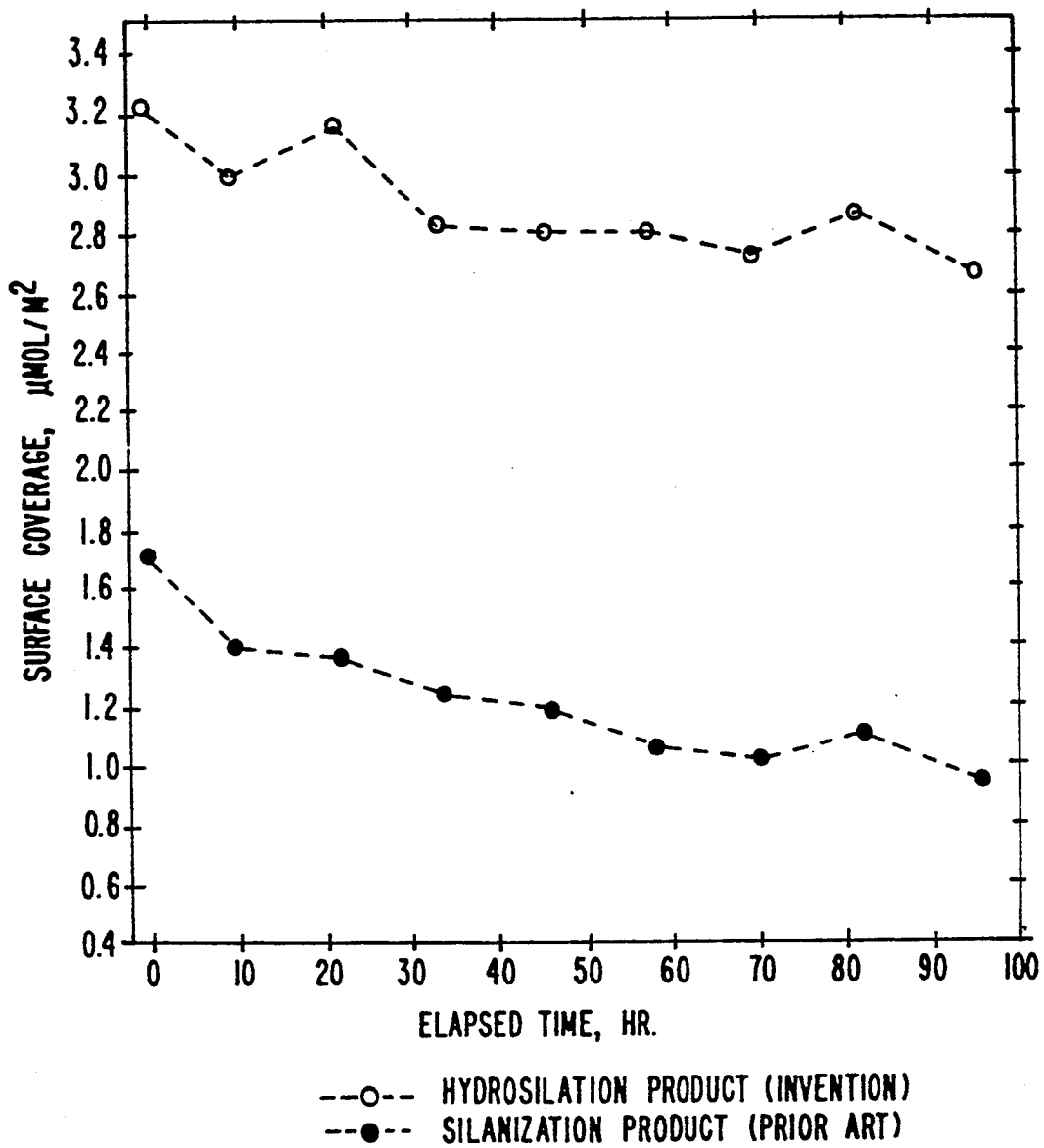
FIG._3.

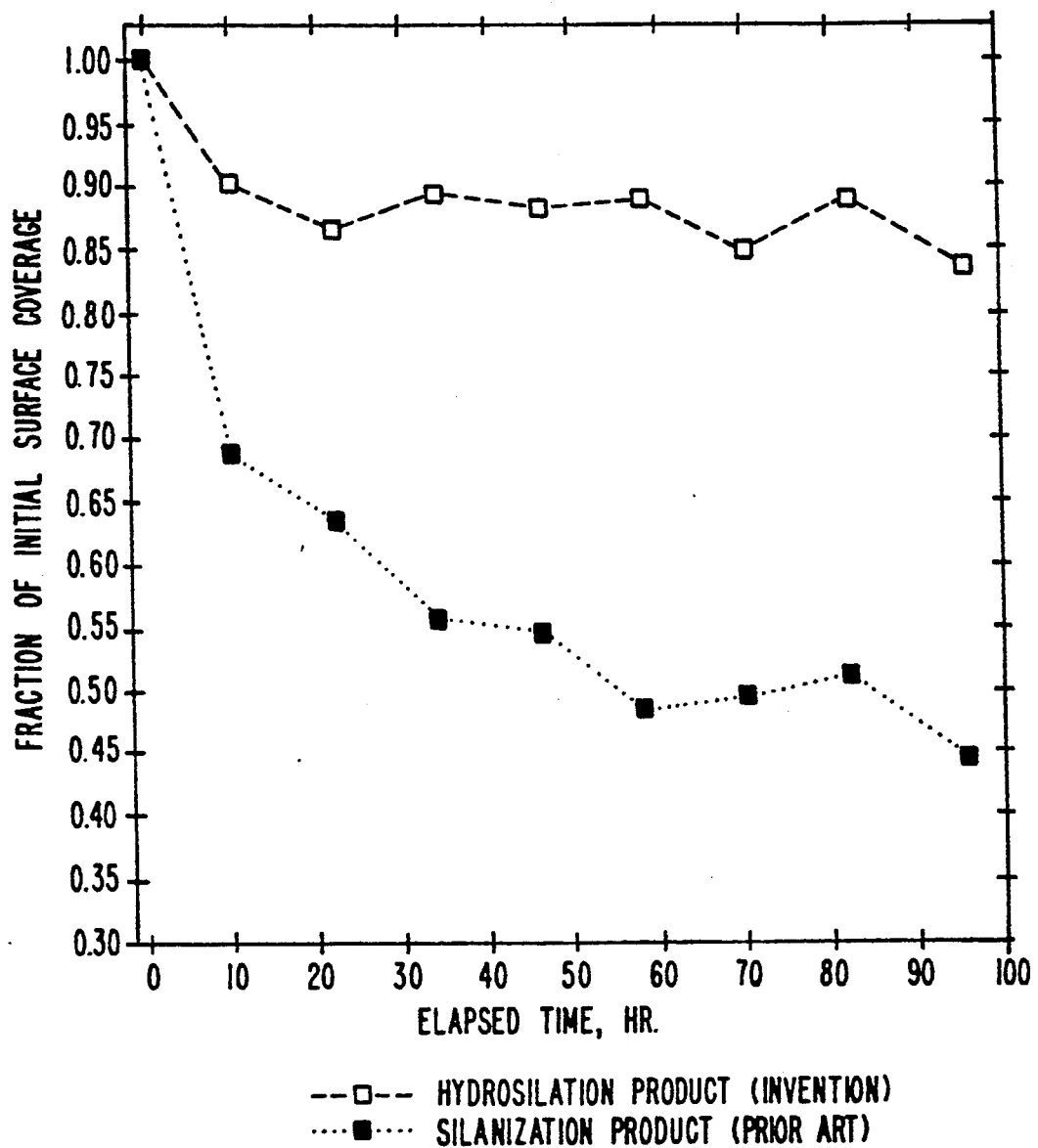
FIG._4.

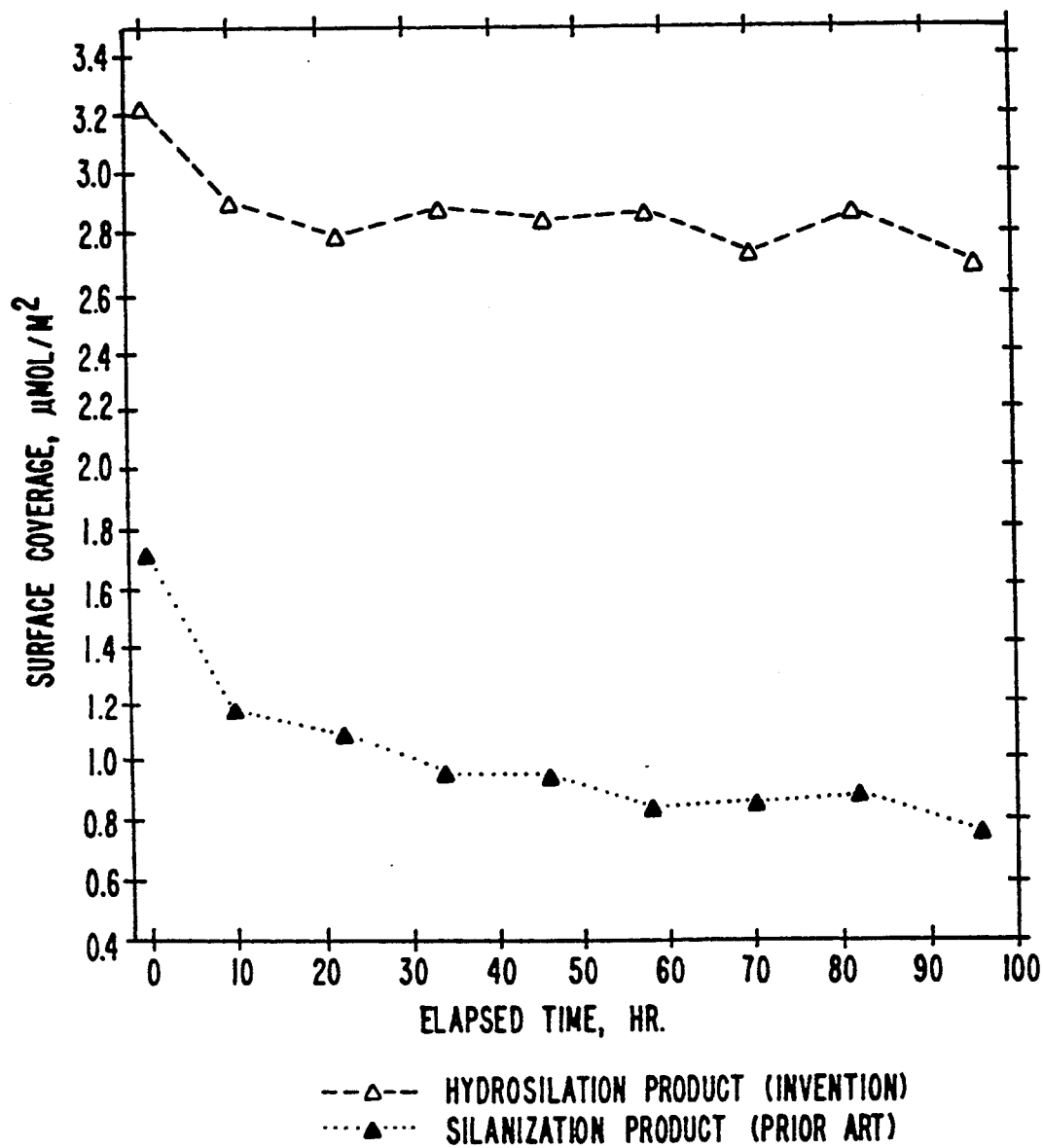
FIG._5.

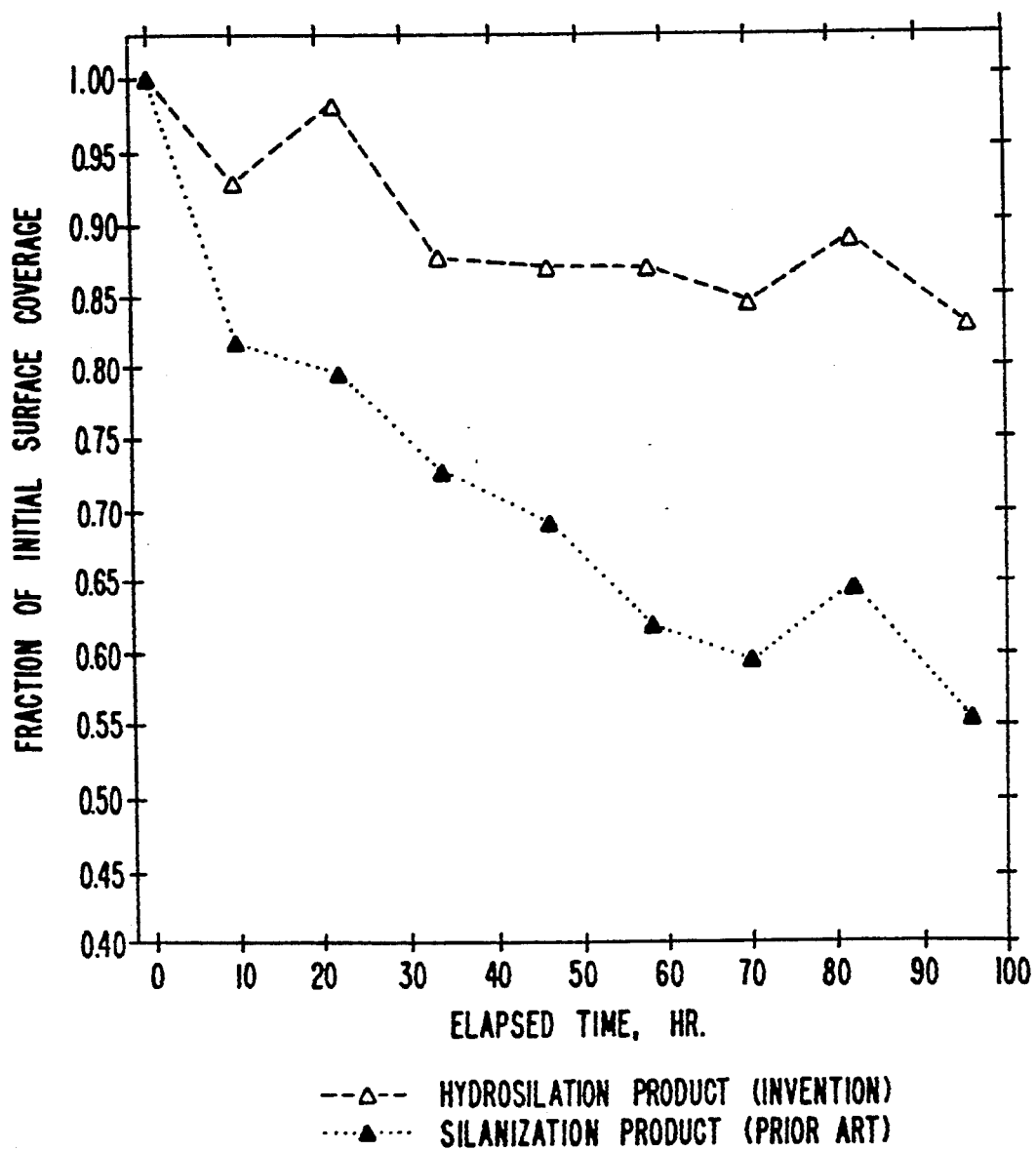
FIG._6.

STABLE, COVALENTLY-BONDED SUPPORTS FOR CHEMICAL SEPARATION APPARATUS MADE THROUGH A HYDRIDE INTERMEDIATE

This is a continuation-in-part of application Ser. No. 07/407,816, filed Sep. 15, 1989 now U.S. Pat. No. 5,017,540.

FIELD OF THE INVENTION

This invention relates to a surface-modified material used in a wide variety of separation applications such as chromatography and electrophoresis.

More particularly, the invention pertains to a chemically modified mineral oxide such as silica, quartz or the like, which exhibits improved hydrolytic stability, larger organic coverage and superior separative capabilities when formed into various forms or shapes, such as porous beads or capillary tubes.

BACKGROUND OF THE INVENTION

Chemically modified silicas have been, and continue to be, widely used as supports in a great variety of chromatographic separations. With the aim of controlling its selectivity while reducing unwanted interactions with one or more compounds, numerous synthetic procedures have been developed to attach organic moieties (R) on the silica surface. Early work on the chemical modification of silica (Halasz and Sebastian, *Angew. Chem.* (Int. Ed.) 8:453 (1969); Deuel et al., *Helv. Chim. Acta* 119:1160 (1959)) described the use of an esterification reaction between surface silanol groups (SiOH) and an alcohol to give a structure of the following type:

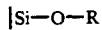

|Si—O—R

Although such materials were useful for many separations, their limited hydrolytic stability seriously precluded the extensive usage of these bonded phases, particularly in liquid chromatography which requires the use of aqueous eluents.

Currently, commercially available bonded phases are prepared by reacting selected organosilanes with the silica surface. Halogen- or alkoxy-substituted alkyldimethylsilanes are the most commonly used silanizing reagents. The resulting bonded support bears monolayer surface structures of the following type:

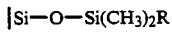

|Si—O—Si(CH₃)₂R

By changing the structure of the R group, it is possible to produce bonded silicas with a great variety of organic groups, ranging from non-polar materials, for instance, octyl- and octadecyl-silicas commonly used as bonded supports in reversed-phase liquid chromatography, to ionic materials such as benzenesulphonic acid derivatives which are widely used in ion-exchange liquid chromatography. The preparation of these and similar materials are described in a number of publications (e.g., Roumeliotis and Unger, *J. Chromatogr.* 149:211 (1978) or Asmus et al. *J. Chromatogr.* 123:109 (1976)) and patents (Sebastian et al. U.S. Pat. No. 3,956,179; Hancok et al. U.S. Pat. No. 4,257,916; or Ramsden et al. U.S. Pat. No. 4661,248).

In a related approach, polymeric (multilayer) bonded stationary phases are prepared from bi- or tri-substituted organosilanes with the general formula $X_nSiR_{4-n}$, where X=alkoxy, halide or any easily hydrolyzed group, and n=2,3. The resulting polymeric bonded support bears repeating surface structures of the type

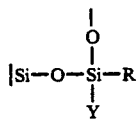

where Y=—R (n=2) or —O— (n=3) and the oxygen atom (—O—) is bonded either to a hydrogen (that is, as part of a free silanol, Si—O—H) or to another silicon atom (that is, as part of a siloxane linkage, Si—O—Si). A number of patents and publications describe the preparation of these materials (Kirkland and Yates, U.S. Pat. Nos. 3,722,181 (1973), and 3,795,313 (1974); Novotny et al., *J. Chromatog.* 83:25 (1973); Sander and Wise, *Anal. Chem.* 56:504 (1984)). Although in many instances these bonded supports provide satisfactory separations, the lack of control of the polymerization process seems to be a major contributor to such problems as irreproducible layer thickness and incomplete silanol condensation. This limitation has confined polymeric bonded stationary phases to applications where the presence of a multilayer is necessary and/or its thickness is relatively unimportant. As a consequence, the vast majority of liquid chromatographic separations are carried out with monolayer bonded phases.

The recent development of electrophoretic separations in a capillary format has promoted the extent of the silanization technology normally used in chromatography to the deactivation of the inner wall of the fused silica capillary. Thus, Jorgenson et al. (*Science* 222:266 (1983)) have noted that separation of model proteins, such as cytochrome, lysozyme and ribonuclease A, in untreated fused silica capillaries with a phosphate buffer at pH 7 was accompanied by severe tailing, and suggested that this might be caused by strong interactions between the proteins and the capillary wall. Derivatization of the capillary wall has been proven effective to prevent or control protein adsorption (McCormick, *Anal. Chem.* 60:2322 (1988); Bruin et al., *J. Chromatog.* 471:429 (1989)). In addition, by chemically modifying the inner surface of the capillary, operational variables such as the electrosomotic flow are more amenable to control. In another application (Hjerten, U.S. Pat. No. 4,680,201 (1987); Cohen and Karger, U.S. Pat. Nos. 4,865,706 and 4,865,707 (1989)), a method is described for preparing fused-silica capillary tubes for electrophoretic separations by use of a bifunctional compound in which one group (usually a terminal —SiX₃ group where X=ethoxy, methoxy or chloride) reacts with the capillary wall and the other (usually an olefin group) does so with a monomer taking part in a polymerization process. This process resulted in a wall-bonded, polymer-filled capillary useful for polyacrylamide gel electrophoresis.

The extensive usage of these bonded materials in chromatography and capillary electrophoresis does not necessarily imply that they meet all requirements with respect to separation performance and stability. On the contrary, monomeric bonded phases, for instance, are subject to serious effects arising primarily from a relatively limited organic coverage due to the "bulky"

methyl groups of the anchored moiety, and from a still unsatisfactory hydrolytic stability of the Si—O—Si—C linkage, particularly under moderately acidic or slightly alkaline elution conditions. Similarly, polymeric bonded phases although having somewhat better organic coverages, contain a considerable population of free silanols and also exhibit a limited hydrolytic stability. Incomplete surface coverage and poor hydrolytic stability both result in the exposure of a substantial number of surface silanols, groups which are known to be primarily responsible for the residual adsorption phenomena that plague silicon-based separation materials. These so called "silanophilic" interactions are usually undesirable in chromatography as well as in capillary electrophoresis because they often result in "tailing" peaks, catalyze solute decomposition, lead to unreliable quantitation, etc. One of the most striking cases of silanophilic interactions occurs perhaps in the separation of certain compounds containing amino or other similar groups, particularly biomolecules. For instance, many proteins may interact very strongly with unreacted silanols leading to excessive band tailing, incomplete recovery of one or more solutes, or even recovery of the same component from different bands.

In an effort to overcome such problems, other organosilane reagents have been developed. Two related approaches have been proposed in which either the methyl groups of the organosilane reagent are replaced by bulkier groups (Glajch and Kirkland, U.S. Pat. No. 4,705,725, (1987)) or a "bidentate" silanizing reagent is used (Glajch and Kirkland, U.S. Pat. No. 4,746,572, (1988)). In both cases the new groups are aimed to shield the unreacted silanols as well as the hydrolytically labile linkage that bonds the silane to the support. Although this steric protection has resulted in somewhat improved bonded phases, the synthetic procedures still involve the formation of unstable Si—O—Si—C linkage, and therefore, the necessity still exists for a truly effective silane chemistry.

In another completely different approach, bonded silicas bearing direct Si—C linkages have been developed. They involve the sequential reaction of the silica substrate with a chlorinating reagent (e.g., thionyl chloride) and a proper alkylating reagent (e.g., a Grignard or organolithium compound):

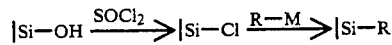

where —M=—Li or —MgBr. In principle, this method should provide not only a closer attachment and a denser coverage of organic functionalities but also a more hydrolytically stable bonded phase than that obtained by the corresponding Si—O—Si—C linkage. However, the acceptance for the application of a chlorination/Grignard or chlorination/organo-lithium reaction sequence as a routine method to modify silica substrates has been hindered by several factors. One factor is that the one-step organosilanization procedure (such as described in U.S. Pat. No. 3,956,179 to Sebastian et al.) is relatively easy to carry out as compared to the two-step halogenation/alkylation sequence. Difficulties associated with the removal of residual salts which may be occluded in the porous silica matrix during the alkylation process is also an important factor which has contributed to the limited usage of this synthetic approach. Finally, but not less importantly, the preparation of the alkylation reagent exhibits strong interferences with many reactive functionalities, particularly those containing carbonyl, nitrile, carboxyl, amide, alcohol, etc. That is, the great reactivity which makes a Grignard reagent so useful in many synthetic approaches seriously limits its applicability. The organic group, R, in the Grignard reagent, RMgBr, must remain intact during the preparation of the reagent. It is a well known fact that Grignard reagents react with acidic components to form the corresponding hydrocarbon group R—H. More strictly, "any compound containing hydrogen attached to an electronegative element such as oxygen, nitrogen, and even triply-bonded carbon are acidic enough to decompose a Grignard reagent" (Morrison and Boyd, *Organic Chemistry*, 3rd Edition, 1974). Additionally, a Grignard reagent reacts readily with molecular oxygen, carbon dioxide, and with "nearly every organic compound containing a carbon-oxygen or carbon-nitrogen multiple bond" (supra). The nitro group (—NO$_2$) also appears to react oxidatively with a Grignard reagent. It seems clear therefore that only a very limited number of organic functionalities may be present in the halide compound from which a Grignard reagent can be prepared. Being even more reactive than the corresponding Grignard reagent, an organolithium reagent should exhibit the same limitations described above to a similar or even greater extent. This, of course, greatly limits the versatility of this approach.

It is therefore desirable to address the shortcomings of existing bonded packings by developing an alternate silane chemistry which combines the superior coverage and hydrolytic stability of direct Si—C linkages with the preparation simplicity of silanization.

SUMMARY OF THE INVENTION

In one aspect of the present invention, a solid intermediate is provided that comprises an inorganic oxide-based, relatively rigid surface. The surface (after final derivatization) is exposable to fluids with components therein being separated, such as during chromatographic or electropheric separations. The intermediate surface before final derivatization has hydride groups thereon.

After final derivatization, supports of the invention have an inorganic oxide substrate to which is covalently attached an organic functionality, through hydrolytically stable surface-to-carbon linkages. A preferred support of this invention comprises a silica substrate which, upon derivatization by methods described in this invention, contains surface structures of the following type:

where R is an alkane, substituted alkane, alkene or substituted alkene.

The present invention represents a totally different approach to the prior problems in producing very stable, covalently bonded separation substrates for all types of liquid and gas chromatography as well as capillary electrophoresis.

Supports of the invention are prepared by the catalytic addition of silicon hydrides to organic compounds bearing a terminal vinyl or acetenyl group via a solid intermediate, which provides the silicon hydride species on the substrate surface. The final product contains closely packed direct silicon-carbon linkages thus providing a significantly improved surface-modified separation support with regard to stability and silanophilic interactions. Additionally, because of the intrinsic freedom from interferences of the catalytic SiH addition (hydrosilation), the method of preparation is an extremely versatile one in that it allows bonding of virtually any organic functionality to a support material, in a clean, high-yield procedure. By properly choosing the chemical composition of the R-group, chemically bonded separation materials may be prepared which exhibit a wide range in selectivity.

BRIEF DESCRIPTION OF THE DRAWINGS

FIG. 1 illustrates partial IR spectra of hydride intermediates prepared according to the invention via a chlorination/reduction sequence, as described in Example 1 (curve A); or by coupling with the acid hydrolysis product of triethoxysilane, as described in Example 2 (curve B);

FIG. 2 illustrates partial IR spectra of octyl- (curve A) and octadecyl-(curve B) bonded silicas prepared according to the invention, as described by Example 3;

FIG. 3 illustrates plots of surface coverage versus hydrolysis time for octyl bonded Vydac 101TPB ™ silicas, one of which (hydrosilation product) was prepared according to this invention and the other (silanization product) from a commercial (prior art) procedure. The long-term hydrolysis was in 15 mM trifluoroacetic acid solution containing 10% v/v dioxane, as described in Example 4;

FIG. 4 is analogous to FIG. 3, but is shown on a relative basis; and

FIGS. 5 and 6 illustrate the same test as FIGS. 3 and 4, but this time the test solution was 15 mM phosphate at pH 2.0.

DETAILED DESCRIPTION OF THE INVENTION

This invention differs from most of the materials currently available by including a direct substrate-to-carbon bond instead of a substrate-O—Si—C type of linkage. It is a primary purpose of this invention to provide a surface-modified separation material which exhibits extended lifetime (hydrolytically stable), displays improved adsorption properties (more extensive and versatile organic coverage), and is substantially free of contaminants (e.g., residual salts and the like).

This unique material of the invention is produced by the catalytic addition of surface hydride species to an organic reagent containing a multiple carbon-to-carbon bond, after converting the original surface hydroxyl to hydride groups. The method of making this surface-modified material is a very versatile one in that it allows the attachment to a substrate of organic functionalities which could not be possible by regular organometallic procedures.

Supports of the invention are produced from a structurally rigid inorganic oxide which provides a hydrated surface vastly populated by hydroxyl groups. Suitable inorganic substrates as precursors include, but are not limited to, oxides of metalloids and metals such as silicon, aluminum, tin, thorium, magnesium, titanium, zirconium, etc., and combinations thereof. In a preferred embodiment, the substrate precursor material is silicon oxide in the form of silica, quartz or the like materials which are commonly used in gas and liquid chromatographic as well as in capillary electrophoretic separations. In two particularly preferred embodiments, the substrate precursors to be modified are porous, particulate silica (such as beads), as well as non-porous, fused silica or quartz capillary tubes.

The products of the present invention are prepared by a modification scheme which comprises two major steps: (1) Attachment of hydride species on the substrate precursor so as to give a fairly stable intermediate; and (2) Reacting said hydrided surface with organic compounds bearing a terminal unsaturated hydrocarbon group, in the presence of a catalyst, whereby direct linkage of said inorganic substrate to carbon is provided.

The hydroxyl groups of the oxide substrate precursor provide active sites which can be chemically transformed into intermediate surface hydride groups. This is accomplished either by direct conversion of the hydroxyl groups to hydride groups via a halogenation/reduction sequence, or more preferably, by condensation of the surface hydroxyl groups with a hydridosilane coupling reagent. In the latter instance, the hydride intermediate is thus obtained as a surface deposition of the trihydroxysilane hydrolysis product from a hydrolyzable trisubstituted silane. However, in either case, a chemically and thermally stable hydride intermediate is obtained in which most of the original hydroxyl groups are replaced by silicon hydride species.

In one procedure the substrate precursor material, e.g., silica, is first reacted with a suitable excess of a halogenating reagent, preferably thionyl chloride, in the presence of an anhydrous solvent such as toluene:

Reduction of the halogenated material is then effected by reaction with a suitable excess of a solution of a metal hydride such as lithium aluminum hydride or its derivatives:

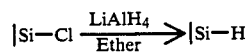

The reduced material is finally subjected to a "clean-up" step with a dilute aqueous acid, so as to remove chemisorbed salts (e.g., aluminum chloride) which originate from the reducing reagent.

A more preferred procedure to prepare the hydride intermediate involves the reaction of the inorganic oxide substrate, e.g., silica, with a suitable excess of a hydridosilane ethereal solution containing dilute mineral acid (typically 0.1 M HCl):

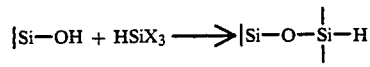

where X is a hydrolyzable group, preferably an alkoxy or halide group such as ethoxy or chloride.

The hydrided surface is then reacted with an organic compound containing a carbon-to-carbon multiple bond, preferentially a terminal vinyl group, in the presence of an appropriate catalyst so as to give a direct linkage of the surface to carbon:

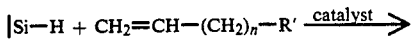

$$|Si-(CH_2)_{n+2}-R'$$

where n≥0 and R'=alkane, substituted alkane, alkene or substituted alkene That is, R' ranges from simple hydrocarbon groups such as n-alkyls to heteroatom compounds such as carbonyls, nitriles, amides, epoxy, etc., depending on the application for which the final addition product —the bonded substrate— is intended. Alternatively, an acetenyl-terminated compound with the general formula HC≡C—(CH$_2$)$_n$—R' can be used.

As previously known in other contexts, the addition of silicon hydrides to unsaturated hydrocarbons, commonly referred to as hydrosilation or hydrosilylation, has been recognized as one of the most important laboratory methods to form Si—C bonds. The reaction's minimal interference with other reactive functionalities (e.g., CO$_2$R, CN, NH$_2$, etc.) has permitted the attachment of silicon to organic molecules which otherwise cannot be introduced by regular organometallic procedures. Details of the reaction in homogeneous phase can be found elsewhere (e.g., Speier, *Adv. Organomet. Chem.* 17:407 (1979); Seyferth, editor, *J. Organomet. Chem. Library* 5:1 (1977)).

Hydrosilation is generally carried out in the presence of a metal catalyst. A variety of inorganic and organic complexes of transition metals such as platinum, rhodium, palladium, ruthenium, iridium and nickel have functioned as very effective catalysts for the addition reaction. The catalyst often consists of a solution of a halide-, olefin-, carbonyl- or phosphine complex of the transition metal. Chloroplatinic acid in an isopropanol solution (also known as "Speiers" catalyst) is the most commonly used form. Only as little as $10^{-5}$ mole of platinum per mole of silicon hydride is normally sufficient for an effective hydrosilation. Commonly, an "induction period" is required when the Speiers catalyst is used. The addition then becomes rapid and can be done at room temperature or under reflux to ensure a high yield.

For simple liquid olefins no additional solvent is normally required. For highly reactive olefins (such as those with a strong tendency to polymerize, e.g., allylmethacrylate, allyl glycidoxyl ether, etc.) an inert solvent such as toluene, benzene, saturated hydrocarbons, chloroform, etc. is suitable. In general, the reaction is conveniently carried out under dry conditions, at temperatures often below the boiling point of the liquid. Typically, an excess of the olefin with respect to the available surface hydride groups is used. The magnitude of such an excess depends on the nature of the substituents in the olefin. Highly reactive reagents (epoxy-containing olefins, for instance) require 10 to 50% molar excess while simple (unsubstituted) olefins may need a 10-fold molar excess or more to produce a high surface coverage.

As with any surface modification procedure, the sites of the bonding reaction will eventually become sterically hindered at some point and, consequently, not all of the Si—H sites will be converted to Si—C. In order to remove as many of the remaining hydrides as possible, a "hydride end-capping" procedure usually follows the primary bonding reaction. Ethylene gas is conveniently used for this purpose since it offers the smallest possible steric hindrance in olefinic addition. Once the main bonding reaction is considered complete, the ethylene gas is introduced into the reactor and maintained at high pressure over the solution containing the bonded support. This mixture is stirred and heated again for a period of several hours. The need for hydride end-capping is particularly critical when aqueous alkaline solutions are used. Under these conditions, hydride groups are rapidly hydrolyzed generating hydrogen gas, with obviously deleterious effects if the reaction occurs during the course of a separation. Under acidic conditions, on the other hand, silicon hydride groups are virtually indefinitely stable and, therefore, hydride end-capping may not be necessary. Compared to conventional silanol end-capping of the prior art in which a bulky trimethylsilyl group, (CH$_3$)$_3$Si—, is attached, hydride end-capping in the present invention results in a "skinny" (linear) ethyl surface ligand, CH$_3$CH$_2$—. A more efficient secondary surface coverage can therefore be expected.

In general, the hydrosilation reaction has a great deal of versatility. This is due to the fact that relatively few reactive functionalities interfere with the olefinic addition. For example, hydrosilations catalyzed by chloroplatinic acid have been used to attach to silicon organic groups containing a wide variety of functionalities including: halogens, nitrite, cyanide, amines, alkylsulfites, alkylsulfonamides, borate esters, and phosphohalides. The ester group (—CO$_2$R) does not normally interfere with the hydrosilation reaction. However, addition to the carbonyl group of aldehydes and ketones usually, although not always, takes place. This seems to be particularly true for α,β-unsaturated carbonyls. A similar behavior is exhibited by unsaturated nitriles as well as epoxydes of 1,3-dienes. By using olefins whose C≡C bond is separated from the heteroatom unsaturation by at least a methylene (—CH$_2$—) group, normal 1,2-addition is readily achieved. Carboxylic acids, phenols and alcohols react at the —OH group, although normal addition can occur with olefinic tertiary and sometimes secondary alcohols in which alcoholysis of the Si—H group is sterically hindered. Acidic functionalities can be bonded to silicon, however, by "protecting" the —OH group with a (CH$_3$)Si— group, which can be readily hydrolyzed off afterwards.

Among the major advantages of the practice of the present invention is that the relatively limited surface coverage due to the "bulky" methyl groups in prior art organosilanes can be avoided and, consequently, a more densely populated surface can be obtained. Additionally, the hydrolytic advantage of direct Si—C linkages may be achieved without the disadvantages that occur when such a linkage is obtained by the known sequential reaction with a chlorinating reagent and an alkylating reagent such as Grignard or organolithium. Moreover, the intrinsic freedom from interference makes hydrosilation a particularly convenient approach to attach virtually any organic functionality to a hydride support, resulting in a remarkably versatile separation material. Thus, the present invention not only combines the superior coverage and hydrolytic stability of direct Si—C linkages with a simplicity approaching that of currently available silanization procedures, but also provides a versatile separation support suitable for virtually any application.

The primary applications for the invention are in the areas of bonded phases for high performance liquid chromatography (HPLC) as well as inner surface-modified capillaries for high performance capillary electrophoresis (HPCE). In both applications the products of the invention will be especially useful for the separation of biologically important solutes such as proteins and nucleic acids as well as their fragments. Very often, HPLC separations of proteins have to be carried out in mobile phases containing aggressive electrolytes at low pH, such as trifluoroacetic acid. Under these conditions bonded supports from the previous art perform poorly with reference to organic phase degradation. Similarly, HPCE separations of proteins in surface-modified capillaries produced by the previous art exhibit "bleeding" of the bonded coating. In any case, this results in either irreproducible results on an analytical scale or in a significant solute contamination on a preparative scale. The products of this invention overcome the degradation disadvantage of prior HPLC and HPCE materials while still providing similar or better separation performance.

In its most preferred form, the organic reagent used in the present invention assumes the general formula $CH_2=CH-(CH_2)_n-G$, where the terminal vinyl group provides attachment to the support surface, the group —G provides the desired functionality, and the value of n controls the length of the chain separating the two groups. The bonded supports of this invention can contain a wide variety of functional groups to fit virtually any application. A few illustrative examples in HPLC include non-polar, purely hydrocarbonaceous —G ligands for "reversed" phases, polar groups such as nitrile ($-C\equiv N$) for "normal" phases, and ionogens such as quaternary ammonium salts and sulfonic acids for anion- and cation-exchange phases respectively.

A particularly important application of the present invention is in affinity chromatography. In this case, the —G functionality assumes a specially reactive form such as epoxy or certain succinimido esters, represented by the following substituted-olefin structures:

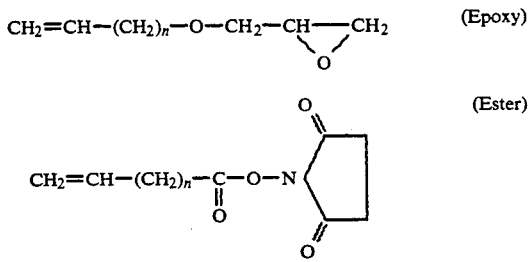

Once bonded to the hydrided substrate, these groups are readily bound to ligands with specific biochemical activity. Of special novelty is the reactive ester because the current art requires a cumbersome, multi-step preparation procedure.

For size-exclusion chromatography, the —G functionality takes the form of hydrophilic groups such as polyols, which can be readily prepared via acid hydrolysis of previously bound epoxy groups. Alternatively the epoxy ring can be opened with a properly sized polyglycol, in which case a polymeric coating will result.

A similar polyol-modified surface can be used in open-tube capillary electrophoresis. In this case the hydrophilic fused-silica capillary is particularly useful for the electrophoretic separation of biopolymers such as proteins and their fragments. In another important HPCE application, an olefinic modifier such as allylmethacrylate (in which $-G=-O-CO-C(CH_3)=CH_2$) can be bonded to the capillary wall. This bonded functionality is then copolymerized with a gel mixture to produce a gel-filled, wall-bonded capillary which is useful for gel HPCE. Extremely high resolving power is achieved with these capillaries when applied to polyacrylamide gels. This technique is particularly well-suited for the separation of biologically important macromolecules including nucleic acids, proteins and their fragments, under both denaturing as well as nondenaturing conditions.

EXPERIMENTAL

Materials and Methods

Toluene, diethyl ether and dioxane (EM Industries, Inc.) were dried by allowing them to stand with calcium hydride (Sigma Chemical Co.) for several days, refluxing and then distilling from the hydride immediately before use. A 0.2 M lithium tetrahydridoaluminate (Sigma Chemical Co.) ether solution was prepared and used as the reducing reagent. Thionyl chloride ("Gold Label" Aldrich Chemical Co ), 1-octene and 1-octadecene (Sigma Chemical Co.) were used as received. Infrared quality potassium bromide (Harshaw/Filtrol Partnership) powder was used for the FT-IR spectra. Two particulate silica substrates were used: Partisil-40 ™ (Whatman Inc., Clifton, N.J.) with a 40 μm mean particle size, 85Å mean pore diameter and 315 m$^2$/g surface area; and Vydac 101TPB ™ (The Separations Group, Hesperia, Calif.) with 5.6 μm mean particle size, 334Å mean pore diameter and 89 m$^2$/g surface area.

All silica derivatization reactions were carried out under a dry nitrogen atmosphere in glassware that had been previously dried at 120° C. overnight. Transfer of liquids was accomplished either with a glass syringe (<20 mL) or by means of a stainless steel cannula and nitrogen pressure, via silicone rubber septa. Prior to reaction, the silica substrate was dried under vacuum at 110° C. overnight and then cooled in a vacuum desiccator.

Infrared spectra were taken in the 4,000–450 cm$^{-1}$ region with a Perkin Elmer Model 1800 FT-IR spectrometer equipped with a Spectra-Tech diffuse reflectance accessory. Silica samples were mixed 1:1 by weight with KBr and 100 sample scans were ratioed against pure KBr as a reference. Spectra shown were normalized to 100% transmittance.

EXAMPLE 1

Preparation of Hydride Silica by a Chlorination/Reduction Sequence 5.00 g of dried Partisil-40 ™ silica were suspended in 60 mL of freshly distilled, dry toluene, and 10 mL of thionyl chloride (to obtain a 10-fold ratio excess with respect to silanol content) were added. The mixture was magnetically agitated and the chlorination was allowed to proceed under reflux for at least 18 hours after which the excess SOCl$_2$ was distilled off. Removal of any remaining SOCl$_2$ was achieved by washing the dark-purple product at least 8 times with 80-mL portions of dry toluene while magnetically stirring for 15 min. After each washing, and once the solid had settled, the solvent was carefully aspirated off to waste by means of a slight vacuum applied to a glass pipette. Finally, the chlorinated silica was washed with one 30-mL portion of dry diethyl ether, and then left in a final fresh ether aliquot.

70 mL of 0.2 M LiAlH$_4$ ether solution (about a 4-fold molar ratio, hydride/original silanol) were added slowly to the chlorinated silica/ether suspension while stirring. An immediate reaction was evidenced by a color change from dark purple to white. The reaction was allowed to proceed for two hours under a gentle reflux. A dry-ice condenser was found to be appropriate to safely condense relatively volatile intermediate reaction byproducts. The excess of LiAlH$_4$ was then aspirated off and destroyed by adding ethyl acetate (about 10 mL) followed by isopropanol dropwise with stirring until hydrogen evolution ceased. The product was next washed with eight 30-mL portions of dry ether to remove any remaining aluminum hydride and/or chloride species in solution. The "hydrided" silica was then dried overnight in a vacuum dessicator at room temperature. The dry solid was washed 3 times with 50 mL portions of a 0.5 M HCl aqueous solution, followed by further washings with tetrahydrofuran (THF)/water 1:1 v/v and ether. The product was finally dried at 110° C. under vacuum overnight. The partial IR spectrum of the hydride intermediate so prepared is illustrated by curve A of FIG. 1.

EXAMPLE 2

Preparation of Hydride Silica by Silane Condensation (Coupling)

Five grams of Partisil-40 ™ silica were suspended in 50 mL of dioxane containing 5 mL of 3 M HCl aqueous solution. The suspension was magnetically stirred, heated at about 75° C. and then 110 mL of a 0.2 M triethoxysilane solution in dioxane were added dropwise (obtaining about 30% molar excess of silane with respect to silanol). The reaction was allowed to proceed under reflux for about 60 minutes after which the suspension was centrifugated and the solid washed consecutively with 50-mL portions of 1:1 v/v THF/water, THF and diethyl ether. After solvent removal, the solid was dried at 110° C. under vacuum overnight.

Except for a favorably higher Si—H surface concentration, the product obtained exhibited essentially identical spectroscopic, chemical and thermooxidative characteristics to that prepared via chlorination/reduction sequence as described in Example 1. The simplicity and efficiency of this procedure make the silane coupling a preferred method. The partial IR spectrum of the hydride intermediate so prepared is illustrated by curve B of FIG. 1.

EXAMPLE 3

Preparation of Octyl- and Octadecyl-Bonded Silicas 60 mL of 1-octene (density 0.715 g/cc, 97% purity) containing 75 μL of 0.1 M chloroplatinic acid solution in 2-propanol were heated to about 70° C. while agitating magnetically for about 30 min or until a clear solution was obtained. Five grams of hydride intermediate substrate prepared as described by Example 1 were then added to the olefin/catalyst solution, and the reaction allowed to proceed for about 24 hours at 100±2° C. The mixture was then centrifugated and the solid washed with three 40-mL portions of toluene followed by similar washings with dichloromethane and diethylether. After removing the solvent, the solid was dried at 110° C. overnight. The octyl-bonded silica contained 10.9% (by weight) of carbon, which corresponds to a surface coverage of about 3.7 μmole of octyl groups per square meter. The use of an equivalent amount of the olefin-platinum complex dicyclopentadienyl platinum(II) dichloride as catalyst resulted in essentially the same level of surface coverage. A partial IR spectrum of the product is shown in curve A of FIG. 2.

A similar procedure, this time with 1-octadecene (density 0.79 g/cc, 99% purity) instead of 1-octene, was followed to prepare an octadecyl-bonded silica. A carbon content of 11.8% (by weight) was obtained which corresponded to a surface coverage of about 1.8 μm/m$^2$. Curve B of FIG. 2 shows a partial IR spectrum of the octadecyl-silica product.

EXAMPLE 4

Long-Term Hydrolysis Test of an Octyl-Silica Prepared According to the Invention Using Vydac 101TPB ™ silica as a substrate, an octyl-bonded silica was prepared by consecutively applying the procedures described in examples 1 and 3.

For the hydrolysis test, 0.75 g of the bonded phase material were suspended in 1 mL of dioxane by magnetically stirring for 5 minutes. Then, 40 mL of an aqueous 15 mM trifluoroacetic acid or 15mM phosphate pH 2.0 solution containing 10% v/v dioxane were carefully added. The mixture was magnetically agitated at room temperature for 12 hours. After this period, a 2-mL aliquot of the well-agitated suspension was taken and the liquid of the remaining mother suspension was removed by centrifugation. A fresh treating solution was added and the hydrolysis continued for a new 12-hour period. After each sampling, the volume of the treating solution is decreased so as to maintain a constant liquid-to-solid ratio during the entire process. The procedure is repeated over a total time of about 100 hours. The silica from each 2-mL aliquot sample was washed consecutively with 3-mL portions of 1:1 v/v THF/water, THF and finally diethylether. The solid was dried at 110° C. under vacuum for several hours and its remaining carbon content determined by a conventional combustion method. The decrease in carbon content (% by weight), or its corresponding molar surface coverage (μmoles/m$^2$), is a direct measure of the loss of bonded material from the support.

For comparison purposes, a parallel test was also instituted on a commercially prepared (via a silanization procedure according to the current art) octyldimethylsilyl-silica. The starting silica support was the same for both the commercial batch and the product of this invention. The plots in FIGS. 3–6 clearly show that the rate of degradation of the silica modified via hydrosilation (present invention) is significantly lower than that of the same substrate modified via silanization (currently available art). At the end of the test, the commercial product had lost about 50% of its initial coverage while, under identical conditions, the hydrosilation product lost only about 15% of its starting coverage material. The improved hydrolytic stability of the product from the present invention over the product from the current art is believed due to the superior strength of the Si—C linkage, as compared to that of prior art Si—Si—C linkages.

It is to be understood that while the invention has been described above in conjunction with preferred specific embodiments, the description and examples are intended to illustrate and not to limit the scope of the invention which is defined by the scope of the appended claims.

We claim:

1. A solid intermediate, useful in chromatographic or electrophoretic separations after derivatization, comprising:
   an inorganic oxide substrate defining a surface and having silicon hydride groups attached to the surface, the surface being exposable to fluids with components therein being separated.

2. The solid intermediate as in claim 1 wherein the inorganic oxide substrate is selected from the group consisting of oxides of silicon, aluminum, zirconium, tin, titanium, and combinations thereof.

3. The solid intermediate as in claim 1 wherein the substrate is a silicon oxide.

4. The solid intermediate as in claim 1 wherein the substrate is particulate silica or fused silica.

5. The solid intermediate as in claim 4 wherein the particulate silica is porous.

6. The solid intermediate as in claim 4 wherein the fused silica is formed as a capillary tube.

7. The solid intermediate as in claim 6 wherein the capillary tube is adapted for gas chromatography or for capillary zone electrophoresis.

8. A solid intermediate useful in chromatographic or electrophoretic separations after derivatization, prepared by the process comprising:
   providing a solid inorganic oxide substrate defining a surface and having surface hydroxyl groups and,
   converting the surface hydroxyl groups to intermediate surface silicon hydride groups by either (a) when the surface hydroxyl groups are silanol groups sequentially halogenating the surface silanol groups and reducing the halogenated moieties to form the silicon hydride groups, or (b) reacting the surface hydroxyl groups with a trihydroxyhydridosilane hydrolysis product from a trisubstituted silane.

9. A solid support, useful in chromatographic or electrophoretic separations, prepared by the process comprising:
   providing a solid intermediate defining a surface and having surface hydroxyl groups;
   converting the surface hydroxyl groups to intermediate surface silicon hydride groups by either (a) when the surface hydroxyl groups are silanol groups sequentially halogenating the surface silanol groups and reducing the halogenated moieties to form the silicon hydride groups, or (b) reacting the surface hydroxyl groups with a trihydroxyhydridosilane hydrolysis product from a trisubstituted silane; and
   reacting the silicon hydride groups of said intermediate with a reagent containing at least one terminal unsaturated hydrocarbon group, in the presence of a metal catalyst.

10. The support as in claim 9 wherein the terminal unsaturated hydrocarbon group is $-CH=CH_2$ or $-C\equiv CH$.

11. The support as in claim 9 wherein the reagent further comprise reactive functionalities selected from the group consisting of hydrocarbons, substituted hydrocarbons, carbonyls, carboxyls, esters, amines, amides, sulfonic acids, and epoxides.

12. A method for preparing a solid support useful for chromatographic and electrophoretic separations comprising:
   providing a solid inorganic substrate defining a surface and having surface hydroxyl groups; and
   converting the surface hydroxyl groups of said substrate to intermediate surface silicon hydride groups by either (a) when the surface hydroxyl groups are silanol groups sequentially halogenating the surface silanol groups and reducing the halogenated moieties to form the silicon hydride groups, or (b) reacting the surface hydroxyl groups with a trihydroxyhydridosilane hydrolysis product from a trisubstituted silane.

13. The method as in claim 12 further comprising:
   reacting the intermediate "surface silicon hydride groups" with a reagent containing at least one terminal unsaturated hydrocarbon group, in the presence of a metal catalyst.

14. The method as in claim 12 wherein the terminal unsaturated hydrocarbon group is $-CH=CH_2$ or $-C\equiv CH$.

15. The method as in claim 12 wherein the reagent further comprises reactive functionalities selected from the group consisting of hydrocarbons, substituted hydrocarbons, carbonyls, carboxyls, esters, amines, amides, sulfonic acids, and epoxides.

* * * * *